US006207862B1

(12) United States Patent
Rozzell, Jr.

(10) Patent No.: US 6,207,862 B1
(45) Date of Patent: *Mar. 27, 2001

(54) PRECURSORS FOR THE PRODUCTION OF CHIRAL 1,3-AMINOALCOHOLS

(75) Inventor: J. David Rozzell, Jr., Burbank, CA (US)

(73) Assignee: Biocatalytics, Inc., Burbank, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/019,390

(22) Filed: Feb. 5, 1998

Related U.S. Application Data

(63) Continuation-in-part of application No. 08/994,163, filed on Dec. 19, 1997.

(51) Int. Cl.$^7$ .................................................. C07C 241/00
(52) U.S. Cl. ............................................ 564/150; 564/151
(58) Field of Search ..................................... 564/150, 151

(56) References Cited

U.S. PATENT DOCUMENTS

| 3,668,199 | 6/1972 | Szmuskovicz | 260/239 B |
| 5,200,561 | 4/1993 | Konya et al. | 564/373 |

OTHER PUBLICATIONS

I. J. Jakovac and J.B. Jones, J. Org. Chem. 44 pp. 2165–2168, 1979.
J. B. Jones and I.J. Jakovac. Org. Synth. Coll. vol. pp. 406–410, 1985.
J. B. Jones and I.J. Jakovac in "Preparative Biotransformations" SM. Roberts, editor, pp. 311–316, 1992.
M. Fétizon et al, Tetrahedron. 31 pp. 171–176, 1975.
G. L. Lemiére et al, Tetrahedron Letters, 26, pp. 4527–4528, 1985.
G. L. Lemiére in "Enzymes as Catalysts for Organic Synthesis", pp. 19–34. M. Schnader, editor, 1986.
Z. Shaked and G. Whitesides, J. Am. Chem. Soc. 102, 7104–7105, 1980.
J. B. Jones and T. Takamura, Canadian Journal of Chemistry, G2, 77–80, 1984.
E. S. Wallis and J. F. Lane, Organic Reactors III, Chapter 7, pp. 267–306, 1949.
P. A. S. Smith, Trans. N.Y. Acad. Sci. 31 pp. 504–515, 1969.
S. Simons, Jr. J. Org. Chem, 38 pp. 414–416, 1973.
W. L. F. Amarego et al, J. Chem. Soc. Perkin Trans. I, 229–2237, 1976.
S. Bittner et al, Tetrahedron Letters, 23 pp. 1965–1968, 1974.
L. Bauer and O. Exnor, Argew. Chem. Int. Edition, 13, pp. 376–384, 1974.
P.A.S. Smith, Organic Reactions III, Chapter 9, pp. 337–338, 1946.
J.H. Saunders und R.J. Slocombe, Chem. Rev., 43, pp. 203–218, 1948.
D.V. Barthorpe in "The Chemistry of the Azido Group," Chapter 7, pp. 397–405, 1971.
J.D. Warren and J.B. Press, Synth. Comm. 10, pp. 107–110, 1980.
CAS Registry No. 14668–73–6, Cyclopentanecarboxylic acid, 2–(hydroxyethyl)–, hydrazide, copyright 1998, but possibly in CAS Registry prior to 1998.
CAS Registry No. 13148–99–7, Cyclohexanecarboxylic acid, 2–(hydroxymethyl)–, hydrazide, cis–, copyright 1998, but possibly in CAS Registry prior to 1998.
Chem Abstracts, vol. 65 No. 5, 7125a. rn=6837–03–2, Aug. 1966.*
Beilsteion Online Printout 172496 and 1724961, rn=100536–75–2, 1959.*
Cas Online Printout, 84:150433, 66:2250, 1975.*
Beilstein 1642094, rn=93030–67–2, 1964.*
Cas Online Printout, 85:177191, 1976.*
CAS Online printout; Beilstein Reg. No. (BRN): 2645271 Beilstein; CAS Reg. No. (RN): 93004–58–1, 1 page, 1975.
Acta Chem. Scand., Ser. B, B41(1), pp. 13–7, Jan. 1987.*
Ann. Chim. (Rome) 56(11) 1358–72, Jan. 1966.*
Bull. Soc. Chim. Fr. (*) 2535–41, Jan. 1966.*
CA:7125(c), Jan. 1966.*
CA:5827(f), Feb. 1967.*

* cited by examiner

Primary Examiner—Samuel Barts
(74) Attorney, Agent, or Firm—Christie, Parker & Hale, LLP

(57) ABSTRACT

The disclosure describes novel precursors for the preparation of chiral 1,3-aminoalcohols. The precursors are chiral 4-hydroxycarboxamides, 4-hydroxyhydroxamic acids, or 4-hydroxyhydrazides produced from chiral gamma-lactones, which in turn are derived from 1,4-diols by stereoselective oxidation. The chiral 4-hydroxycarboxamides, 4-hydroxyhydroxamic acids, or 4-hydroxyhydrazides are converted into chiral 1,3-aminoalcohols by stereospecific rearrangement.

14 Claims, No Drawings

PRECURSORS FOR THE PRODUCTION OF CHIRAL 1,3-AMINOALCOHOLS

This patent application is a continuation-in-part of U.S. patent application Ser. No. 08/994,163 entitled "Method for the Production of Chiral 1,3-Aminoalcohols," filed Dec. 19, 1997. U.S. patent application Ser. No. 08/994,163 discloses a method for the production of chiral 1,3-aminoalcohols, an important class of compounds which have applications as pharmaceutical and agricultural intermediates and chiral auxiliary agents. The present invention relates to novel precursors for the production of chiral 1,3-aminoalcohols using the method disclosed in U.S. patent application Ser. No. 08/994,163.

INTRODUCTION

1. Field of the Invention
2. Background and Description of the Prior Art

Chiral 1,3-aminoalcohols are important intermediates in the synthesis of various pharmaceutical products and product candidates, yet the preparation of these compounds remains a significant synthetic challenge to chemists. Gaining control over the stereochemistry of chiral centers at both the alcohol and amine (or in the cases in which only the alcohol- or amine- bearing carbon is chiral, a single chiral center) is the key to the production of these important chemical intermediates.

Chiral 1,3-aminoalcohols have potential applications both as pharmaceutically active compounds, agricultural chemicals, chiral intermediates, and chiral auxiliary agents. For example, U.S. Pat. No. 3,668,199 describes novel 1,3-aminoalcohols having potential applications as anti-diabetic agents and diuretics. In the preparation of these compounds according to the method described in U.S. Pat. 3,668,199, a diketone is first converted into a keto-enamine, followed by catalytic hydrogenation of the keto-enamine using a platinum catalyst or similar. This method has the limitation that the 1,3-aminoalcohols are not produced in optically-pure form and the amino group must be a dialkylamine. U.S. Pat. No. 5,200,561 describes a process for producing optically active amines, including aminoalcohols. This method reacts an oxime with a metal borohydride compound complexed to a different optically-active amine. This method is costly, and further, requires that another optically active amine be used to form the borohydride complex in order to produce the desired optically active amine. Classical methods involving the formation of diastereomeric salts may also be employed to produce optically active 1,3-aminoalcohols; these resolution procedures require the use of an optically active acid to form the diastereomeric salt. The maximum theoretical yield in this method is only 50%, and in actual practice the yield is significantly lower. Thus, previously-described methods for the production of 1,3-aminoalcohols have limitations in scope, efficiency, chiral purity, and yield. An efficient method for the production of 1,3-aminoalcohols of high optical purity would facilitate the production of a number of pharmaceutical intermediates and chiral auxiliaries, and would be greatly desired.

U.S. patent application Ser. No. 08/994,163 describes an efficient method for the production of chiral 1,3-aminoalcohols. Central to the practice of this method is the production of novel intermediates which are precursors of chiral 1,3-aminoalcohols. The present invention, which is a continuation-in-part of U.S. patent application Ser. No. 08/994,163, describes novel precursors useful for the production of chiral 1,3-aminoalcohols.

DETAILED DESCRIPTION OF THE INVENTION

This invention describes key precursors for the production of chiral 1,3-aminoalcohols and methods for their synthesis. These precursors are chiral 4-hydroxycarboxamides, 4-hydroxyhydroxamic acids, or 4-hydroxyhydrazides produced from chiral gamma-lactones, which in turn are derived from 1,4-diols by stereoselective oxidation. The importance of these precursors as intermediates for the production of chiral 1,3-aminoalcohols lies in their ability to be converted via stereospecific rearrangement into chiral 1,3-aminoalcohols with retention of configuration at the carbon ultimately bearing the amine through either the Hofmann Rearrangement (in the case of chiral 4hydroxycarboxamides); the Lossen Rearrangement (in the case of chiral 4-hydroxyhydroxamic acids); or the Curtius Rearrangement (in the case of chiral 4-hydroxyhydrazides). An important aspect of this invention is the broad scope with which the compounds described herein may be employed to produce a broad range of chiral 1,3-aminoalcohols, both cyclic and acyclic, substituted or unsubstituted, bearing aromatic, aliphatic, or heterocyclic groups, in high stereochemical purity. The compounds of the present invention may be used to produce 1,3-aminoalcohols in which both the carbon atom bearing the amino group and the carbon atom bearing the hydroxy group are chiral, or alternatively, 1,3-aminoalcohols in which only the carbon bearing the amino group or the carbon bearing the hydroxy group is chiral.

Central to the synthesis of chiral 1,3-aminoalcohols by the method described in U.S. patent application Ser. No. 08/994163 is the novel combination of three steps, each of which proceeds with a well-defined and controllable stereochemical outcome. The first step is the stereoselective oxidation of a 1,4-diol to the corresponding chiral gamma-lactone using an alcohol dehydrogenase. The 1,4-diol used in the practice of the present invention is preferably substituted at the 2-position or at both the 2- and 3-positions as shown in Figure 1.

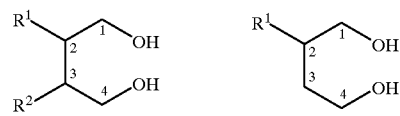

Figure 1: Structures of 1,4-Diols

The substitution is represented in the figure by $R^1$ and $R^2$, which may be selected independently from the substituent groups alkyl, alkenyl, cycloalkyl, cycloalkenyl, cycloalkylalkyl, cycloalkylalkyl, alkynyl, aryl, aralkyl, and heterocyclic ring system. $R^1$ and $R^2$ may also together form a cycloalkyl, cycloalkenyl, or heterocyclic ring system, for example, as in the compound 1,2-cyclohexane dimethanol or 1,2-cyclopentane dimethanol. In cases where $R^1$ and $R^2$ are identical and the diol is a meso compound, the yield of the resulting 1,3-aminoalcohol produced by the method of the present invention can approach 100% of theoretical.

As utilized herein, the term "alkyl," alone or in combination, means a straight-chain or branched-chain alkyl group containing from 1 to about 12 carbon atoms. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of such alkyl groups include methyl, ethyl, chloroethyl, propyl, isopropyl, butyl, isobutyl, tertiary-butyl, 3-fluorobutyl, 4-nitrobutyl, 2,4-dibromobutyl, pentyl, isopentyl, neopentyl, 3-ketopentyl, hexyl, 4-acetamidohexyl, 3-phosphonoisohexyl, 4-fluoro-5,5-dimethylpentyl, 5-phosphinoheptyl, octyl, nonyl dodecyl, and the like.

As utilized herein, the term "alkenyl," alone or in combination, means a straight-chain or branched-chain hydrocarbon group containing one or more carbon-carbon double bonds and containing from 2 to about 18 carbon atoms. Any of the carbon atoms may be substituted with one or more substituents selected from alkoxy, acyloxy, acylamido, halogen, nitro, sulfhydryl, sulfide, carboxyl, oxo, seleno, phosphate, phosphonate, phosphine, and the like. Examples of such alkenyl groups include ethenyl, propenyl, allyl, 1,4-butadienyl, 2-pentenyl, 3-pentenyl, 4-pentenyl, 2,6-decadienyl, 2-fluoropropenyl, 2-methoxypropenyl, 2-carboxypropenyl, 3-chlorobutadienyl, and the like.

As utilized herein, the term "cycloalkyl," alone or in combination, means an alkyl group which contains from about 3 to about 12 carbon atoms and is cyclic. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of cycloalkyl groups include cyclopropyl, cyclobutyl, cyclopentyl, cyclohexyl, cycloheptyl, 2-methylcyclopentyl, 3-methylcyclohexyl, various substituted derivatives, and the like.

As utilized herein, the term "cycloalkenyl," alone or in combination, means an alkenyl group which contains from about 3 to about 12 carbon atoms and is cyclic.

Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of cycloalkyl groups include cyclopropenyl, cyclobutenyl, cyclopentenyl, cyclohexenyl, cyclohexadienyl, cydoheptenyl, 2-methylcyclopentenyl, 3-methylcyclohexenyl, 3-chlorocyclohexenyl, 3-carboxymethylcyclopentenyl, and the like.

As utilized herein, the term "cycloalkylalkyl," alone or in combination, means an alkyl group as defined above which is substituted by a cycloalkyl group containing from about 3 to about 12 carbon atoms. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of cycloalkyl groups include cydopropyl, cyclobutyl, cyclopentyl, cyclohexyl, cycloheptyl, 2-methylcyclopentyl, 3-methylcyclohexyl, 3-fluoromethylcyclohexyl, 3-carboxymethylcyclohexyl, 2-chloro-3-methylcyclopentyl, and the like.

As utilized herein, the term "cycloalkylalkyl," alone or in combination, means an alkyl group as defined above which is substituted with a cycloalkenyl group containing from about 3 to about 12 carbon atoms. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of cycloalkenylalkyl groups include cyclopropenyl, cyclobutenyl, cyclopentenyl, cyclohexenyl, cycloheptenyl, 2-methylcyclopentenyl, 3-methylcyclohexenyl, 3-fluoromethylcyclohexenyl, 3-carboxymethylcyclohexenyl, 2-chloro-3-methylcyclopenentyl, 3-nitrocyclohexenyl, and the like.

As utilized herein, the term "alkynyl," alone or in combination, means a straight-chain or branched-chain hydrocarbon group containing one or more carbon-carbon triple bonds and containing from 2 to about 18 carbon atoms. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of such alkenyl groups include ethynyl, propynyl, 1,4-butadiynyl, 3-pentynyl, 2,6-decadiynyl, 2-fluoropropynyl, 3-methoxy-1-propynyl, 3-carboxy-2-propynyl, 3-chlorobutadiynyl, and the like.

As utilized herein, the term "aryl," alone or in combination, means a carbocyclic aromatic system containing 1, 2, or 3 rings, wherein such rings may be attached in a pendent manner to each other or may be fused to each other. Examples of aryl groups include phenyl, naphthyl, biphenyl, and the like, which may optionally be substituted at any available ring position with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of such aryl groups include phenyl, 4-fluorophenyl, 2-chloroethyl, 3-propylphenyl, 1-naphthyl, 2-naphthyl, 2-methoxy-1-naphthyl, 3,4-dimethoxyphenyl, 2,4-difluorophenyl, and the like.

As utilized herein, the term "aralkyl," alone or in combination, means an alkyl group as defined above which is substituted with an aryl group as defined above. Examples of aralkyl groups include benzyl, 2-phenylethyl, 2,4-dimethoxybenzyl, 4-fluorobenzyl, 4-chlorobenzyl, 4-bromobenzyl, 4-iodobenzyl, m-hydroxy-3-phenylpropyl, 2-(2-naphthyl)ethyl and the like.

As utilized herein, the term "heterocyclic ring system," alone or in combination, means a saturated or partially unsaturated monocyclic, bicyclic, or tricyclic group containing one or more heteroatoms as ring atoms, said heteroatoms selected from oxygen nitrogen, sulfur, phosphorous, selenium, and silicon. Any of the carbon atoms in the heterocycle may be optionally substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of such heterocyclic ring systems include imidazoyl, oxazolinyl, piperazinyl, pyrollidinyl, phthalimidoyl, maleimidyl, thiamorpholinyl, various substituted derivatives, and the like.

The oxidation of the 1,4-diol to the corresponding chiral gamma-lactone occurs by way of formation of the intermediate lactone (which is in equilibrium with the ring-open 4-hydroxyaldehyde form), which is further oxidized, either by the alcohol dehydrogenase or chemically to the lactone. Some examples of oxidation of 1,4-diols to the corresponding chiral lactones catalyzed by horse liver alcohol dehydrogenase is described in J. B. Jones and I. J. Jakovac, *J. Org. Chem.*, 44, 2165 (1979); J. B. Jones and I. J. Jakovac, *Org. Synth.* 63, 10 (1985); and Preparative *Biotransformations* (S. M. Roberts, editor), Chapter 3, pages 3.1.1–3.1.6, John Wiley & Sons, Chichester, U.K. (1997), all hereby incorporated by reference.

In some cases the intermediate chiral lactone may be isolated and oxidized chemically to the gamma-lactone. One method for effecting this oxidation uses silver carbonate on Celite as the oxidizing agent; this method is described by Fetizon et al in *J. Chem Soc. Chem Comm.*, 1118 (1969) and *Tetrahedron*, 31,171 (1975), both hereby incorporated by reference.

Alcohol dehydrogenases used in the practice of this invention require cofactors such as nicotinamide adenine dinucleotide (NAD+) or nicotinamide adenine dinucleotide phosphate (NADP+). A requirement for carrying out the oxidation of a 1,4-diol to the corresponding chiral gamma-lactone at a reasonable cost is the recycling of the NAD+ or NADP+ cofactor. Numerous methods for the recycling of these cofactors are well-known in the art, and any of these methods may be used in the practice of this invention. Some of the methods for recycling NAD+ and NADP+ cofactors are described in G. L. Lemiere, J. A. Lepoivre, and F. C. Alderweireldt, *Tetrahedron Letters*, 26, 4257 (1985); in "Enzymes as Catalysts for Organic Synthesis," pp. 19–34, M. Schneider, Ed., Reidel Dordecht, 1986; Z. Shaked and G. M. Whitesides, *J. Am. Chem. Soc.* 102, 7104–5 (1980); J. B. Jones and T. Takamura, *Can. J. Chem.* 62, 77 (1984); all hereby incorporated by reference. A recycling method described in *Preparative Biotransformations* (S. M. Roberts, editor), Chapter 3, pages 3.1.1–3.1.6, John Wiley & Sons, Chichester, U.K. (1997) uses flavin mononucleotide (FMN), which transfers electrons to oxygen as the ultimate oxidant. In the use of this method, an amount of about 0.0001 moles to about 0.05 moles of NAD+ or NADP+ is used per mole of diol to be oxidized, providing a recycle number for the cofactor of from about 20 to about 10,000.

Some alcohol dehydrogenases useful in the practice of this invention include yeast alcohol dehydrogenase, horse liver alcohol dehydrogenase, bacterial alcohol dehydrogenase from *Thermoanaerobium brockii*, bacterial alcohol dehydrogenase from *Lactobacillus kefir*, alcohol dehydrogenases sold under the ThermoCat trademark by ThermoGen, Inc., alcohol dehydrogenase sold under the SEC ADH name by Biocatalysts Ltd., and many others. By using alcohol dehydrogenases with differing substrate ranges and different stereoselectivity, different stereoisomers of a variety of chiral gamma-lactones may be produced. For example, the alcohol dehydrogenase from *Lactobacillus kefir* (Sigma) has the opposite stereoselectivity from horse liver alcohol dehydrogenase (Sigma, Boehringer Mannheim), and its use in the present invention produces 1,3-aminoalcohols and their precursors with the opposite stereochemistry from those produced by horse liver alcohol dehydrogenase.

In accord with this invention, oxidation of a 1,4-diol to the corresponding chiral gamma-lactone may be conveniently carried out using isolated alcohol dehydrogenase enzymes or using whole cells containing alcohol dehydrogenases enzymes. In the case where isolated alcohol dehydrogenase enzymes are used, these enzymes may be used either as crude, partially purified, or pure preparations. Alcohol dehydrogenases useful in the practice of this invention may be isolated and purified, if desired, from microorganisms capable of effecting the stereoselective oxidation. The purification of the dehydrogenase enzymes may be accomplished by techniques well known to those skilled in the art. Some examples of purification methods for enzymes may be found in *Methods in Enzymology*, 22 (1971) and references therein, hereby incorporated by reference.

These enzymes may be used in solution or, if desired, as immobilized enzymes in accord with the practice of this invention. A number of methods of immobilization for both whole cells containing enzymes and for isolated enzymes are known in the prior art and may be used in the practice of this invention. One example of an immobilized enzyme system is described by Weetall et al., *Methods in Enzymology* 34, 59–72 (1974) which is hereby incorporated by reference. In this method enzymes may be immobilized on a porous glass or ceramic support which has been activated with glutaraldehyde. Other methods for immobilization of both cells and enzymes which may be used in the practice of this invention are described in *Methods in Enzymology* 44(1976), K. Mosbach editor, *Immobilization of Enzymes and Cells*, Gordon F. Bickerstaff, ed., Humana Press, Totowa, N.J. (1997) and in *Biocatalytic Production of Amino Acids and Derivatives*, D. Rozzell and F. Wagner, Eds., Hanser Publishers, Munich, (1992) pp. 279–319.

When whole cells containing alcohol dehydrogenases enzymes are used to catalyze the oxidation of a 1,4-diol to the corresponding chiral gamma-lactone, the addition of a cofactor is not required, as the cell supplies the necessary cofactor. Commonly, when whole cells are used in the practice of this invention, a carbon source such as glucose is added to the medium to supply energy to the cell for maintenance and regeneration of the cofactor. Cells useful in the practice of this invention include the same organisms from which useful alcohol dehydrogenases may be isolated, including Baker's yeast, *Lactobacillus kefir, Thermoanaerobium brockii*, and many other microorganisms which are known to carry out stereoselective ketone reduction or alcohol oxidation or which produce an alcohol dehydrogenase.

The presursors of the present invention are generated in the second step of the reaction sequence: treatment of the chiral gamma-lactone with hydrazine, hydroxylamine, or ammonia under conditions permitting the formation of the corresponding chiral 4-hydroxycarboxamide, 4-hydroxyhydroxamic acid, or 4-hydroxyhydrazide. Conversion of the chiral gamma-lactone to its 4-hydroxyamide, 4-hydroxyhydroxamic acid or 4-hydroxyhydrazide derivative may be accomplished by chemical methods well known to those skilled in the art. For example, heating of a chiral gamma-lactone with ammonia, hydrazine, or hydroxylamine in ethanol produces the corresponding amide, hydrazide, or hydroxamic acid in high yield, and without affecting the chirality at the carbon bearing the carboxyl group. In addition to ethanol, other solvents that may be used in the practice of this invention include isopropanol, n-butanol, t-butanol, dimethylformamide, methyl t-butyl ether, ethyl acetate, butyl acetate, and the like. Alternatively, conversion of the gamma-lactone to the amide, hydroxamic acid or hydrazide may be accomplished by enzymatic catalysis. Esterase, lipase, protease, and amidase enzymes, which can catalyze the hydrolysis of esters in the presence of water, will catalyze conversion of the ester to the amide, hydroxamic acid or hydrazide when ammonia, hydroxylamine or hydrazine are present as nucleophiles. The enzymatic conversion has the added advantage that it often can be carried out under very mild conditions (e.g. ambient temperature and pressure). Further, in certain cases, the enzyme can provide additional stereoselectivity, if desired, in the conversion of the gamma-lactone to its corresponding amide, hydroxamic acid or hydrazide derivative, further improving the enantiopurity of the final product. Some esterases and lipases useful in the conversion of a chiral gamma-lactone to its amide, hydroxamic acid, or hydrazide derivative include *Candida antarctica* lipase (Boehringer Mannheim), *Candida rugosa* lipase (Amano), *Mucor miehei* lipase (Boehringer Mannhiem), esterases sold under the ThermoCat trademark by ThermoGen, Inc., esterases sold by Diversa under the CloneZyme trademark, various proteases and peptidases sold by Sigma, Boehringer Mannheim, Novo, Genencor, and many others. These esterases, lipases, amidases, peptidases, and proteases may also be immobilized as described for the alcohol dehydrogenases using methods well known in the art, if desired.

The third step in the method of the present invention is the stereospecific conversion of the chiral 4-hydroxycarboxamide, 4-hydroxyhydrazide, or 4-hydroxyhydroxamic acid to the corresponding chiral 1,3-aminoalcohol. This conversion may be carried out on the amide under conditions described for the Hofmann Rearrangement, on the hydroxamic acid under conditions described for the Lossen rearrangement, and on the hydrazide under conditions described for the Curtius Rearrangement. These rearrangements are well known in the art. In particular, the stereochemical course of these rearrangements has been well studied, and they have been shown to take place with retention of stereochemistry at the carbon bearing the carbonyl group.

Examples of procedures for carrying out the stereospecific rearrangement on the carboxamide via the Hofmann rearrangement are described in E. S. Wallis and J. F. Lane, *Organic Reactions* III, 267 (1949) and references therein; P. A. S. Smith, *Trans. N.Y. Acad. Sci.* 31, 504 (1969) and references therein; S. Simons, *J. Org Chem.* 38, 414 91973) and references therein; W. L. F. Armarego et al, *J. Chem. Soc. Perkin Trans.* I, 2229 (1976) and references therein; all hereby incorporated by reference. Examples of procedures for carrying out the stereospecific rearrangement on the hydroxamic acid via the Lossen rearrangement are described in S. Bittner et al (Tet. Lett. 23, 1965–8 (1974) and references therein; L. Bauer and O. Exner, *Angew. Chem. Int. Ed.* 13, 376 (1974) and references therein; all hereby incorporated by reference. Examples of procedures for carrying out the stereospecific rearrangement on the hydrazide via the Curtius rearrangement are described in P. A. S. Smith, Organic Reactions III, 337 (1946) and references therein; J. H. Saunders and R. J. Slocombe, *Chem. Rev.* 43, 205 (1948) and references therein; D. V. Banthorpe in *The Chemistry of the Azido Group*, S. Patai Ed., Interscience, New York, 1971, pp. 397–405 and references therein; J. D. Warren and J. D. Press, *Synth. Comm.* 10, 107 (1980) and references therein; all hereby incorporated by reference. When an acyl halide or similar is used to activate the N-hydroxy group in the Lossen rearrangement, acylation of the alcohol also occurs, producing an ester of the chiral 1,3-aminoalcohol as the rearrangement product. The ester of a chiral 1,3-aminoalcohol may also be a useful intermediate in chiral synthesis. This chiral ester may be hydrolyzed, if desired, to the corresponding chiral 1,3-aminoalcohol by methods well known in the art.

Examples of chiral 4-hydroxyamides, 4-hydroxyhydrazides, and 4-hydroxyhydroxamic acids of the present invention are represented by the chemical formula in Figure 2,

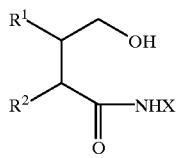

Figure 2. General Structure of Precursors for Chiral 1,3-Aminoalcohols
wherein X is either H, OH, or $NH_2$ and $R^1$ and $R^2$ are selected independently from the substituent groups hydrogen, alkyl, alkenyl, cycloalkyl, cycloalkenyl, cycloalkylalkyl, cycloalkenylalkyl, alkynyl, aryl, aralkyl, and heterocyclic ring system, except that $R^1$ and $R^2$ are not both hydrogen. $R^1$ and $R^2$ may also together form a cycloalkyl, cycloalkenyl, or heterocyclic ring system, for example, as in the compound 2-hydroxymethyl-1-cyclohexanecarboxamide (X=H), 2-hydroxymethyl-1-cyclopentanecarboxylic hydrazide (X=$NH_2$), or 2-hydroxymethyl-1-cyclopentanecarboxylic hydroxamic acid (X=NHOH).

When meso-diols are used as the starting material for the method of the present invention, a single stereoisomer of a chiral 1,3-aminoalcohol can be obtained in yields approaching 100% of theoretical. For example, cis-1,2-cyclohexane dimethanol may be converted into (1S,2R)-1-amino-2-(hydroxymethyl)cyclohexane via the key precursors (1S,2R)-2-hydroxymethyl-1-cyclohexanecarboxamide (Hofmann Rearrangement), (1S,2R)-2-hydroxymethyl-1-cyclohexanecarboxylate hydroxamic acid (Lossen Rearrangement), or (1S,2R)-2-hydroxymethyl-1-cyclohexanecarboxylate hydrazide (Curtius Rearrangement). Meso-2,3-dimethyl 1,4-butanediol may be converted into (2S,3S)-2-methyl-3-aminobutan-1-ol via the key precursors (2S,3R)-2,3-dimethyl-4-hydroxybutyramide (Hofmann Rearrangement), (2S,3R)-2,3-dimethyl-4-hydroxybutanoic hydroxamic acid (Lossen Rearrangement), or (2S,3R)-2,3-dimethyl-4-hydroxybutanoic hydrazide (Curtius Rearrangement).

As described earlier, when an acyl halide or similar is used to activate the N-hydroxy group in the Lossen rearrangement, a novel group of intermediates is formed by acylation of both the alcohol and the N-hydroxy group of the hydroxamic acid. The generalized structure of this group of novel intermediates is shown in FIG. 3 below, wherein $R^1$ and $R^2$ are selected independently from the substituent groups hydrogen, alkyl, alkenyl, cydoalkyl, cycloalkenyl, cycloalkylalkyl, cycloalkenylalkyl, alkynyl, aryl, aralkyl, and heterocyclic ring system, except that $R^1$ and $R^2$ are not both hydrogen, or $R^1$ and $R^2$ together form a cycloalkyl, cycloalkenyl, or heterocyclic ring system, and $R^3$ is either alkyl or aryl.

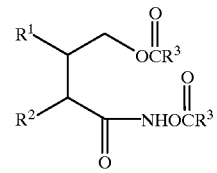

Figure 3. Intermediates in the Lossen Rearrangement

These intermediates may either be rearranged to chiral 1,3-aminoalcohol esters directly without isolation, or, if desired, they may be first isolated prior to rearrangement to the chiral 1,3-aminoalcohol ester. Rearrangement is effected by procedures well known in the art such as by heating in a suitable solvent. Examples of precursors of this type useful in the practice of the present invention include (S)-2-benzyl-4-benzoyloxy-N-benzoyloxybutyramide, (S)-2-benzyl-4-acetoxy-N-acetoxybutyramide, (2R,3S)-2,3-dimethyl-4-acetoxy-N-acetoxybutyramide, (2R,3S)-2,3-dimethyl-4-benzoyloxy-N-benzoyloxybutyramide, (R)-2-(4-fluorophenyl)-4-benzoyloxy-N-benzoyloxybutyramide, and (R)-2-(4-fluorophenyl)-4-acetoxy-N-acetoxybutyramide.

The chiral 1,3-aminoalcohol esters formed on Lossen Rearrangement in the presence of an acyl halide may be isolated by methods well known in the art, or hydrolysed in situ to produce chiral 1,3-aminoalcohols, as earlier described. The generalized structure of this group of compounds is shown in FIG. 4 below, wherein $R^1$ and $R^2$ are selected independently from the substituent groups hydrogen, alkyl, alkenyl, cycloalkyl, cydoalkenyl, cycloalkylalkyl, cycloalkenylalkyl, alkynyl, aryl, aralkyl, and heterocyclic ring system, except that $R^1$ and $R^2$ are not both hydrogen, or $R^1$ and $R^2$ together form a cycloalkyl, cycloalkenyl, or heterocyclic ring system, and $R^3$ is either alkyl or aryl.

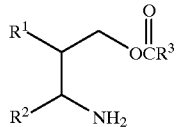

Figure 4. Chiral 1,3-Aminoalcohol Esters

Examples of chiral 1,3-aminoalcohol esters useful in the practice of the present invention include (S)-1-benzyl-3-hydroxypropylamine benzoate ester, produced in the Lossen rearrangement of (S)-2-benzyl-4-hydroxybutanoic hydroxamic acid in the presence of benzoyl chloride, (R)-1-(4-fluorophenyl)-3-hydroxypropylamine benzoate ester, produced in the Lossen Rearrangement of (R)-2-(4-fluorophenyl)-4-hydroxybutanoic hydroxamic acid in the presence of benzoyl chloride, and (2R,3S)-2,3-dimethyl-4-acetoxy-N-acetoxybutyramide, produced in the Lossen Rearrangement of (2R,3S)-2,3-dimethyl-4-hydroxybutyric hydroxamic acid in the presence of acetyl chloride.

The invention will now be further described by the following examples, which are given here for illustrative purposes only and are not intended to limit the scope of the invention.

EXAMPLE 1

Oxidation of cis-1,2-cyclohexane dimethanol to (1R,6S)-(+)-8-oxabicyclo[4.3.0]nonan-7-one Glycine (18.8 grams) is dissolved in 2 liters of deionized water, and the pH is adjusted by the addition of 10% sodium hydroxide to 9.0. Cis-1,2-cyclohexane dimethanol (10.0 grams) is added to the glycine solution with stirring until dissolution occurs, followed by the addition of β-NAD+ (Sigma, 2 grams) and flavin mononucleotide (Sigma, 30 grams). To the resulting clear orange solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent 1:1 ethyl acetate-methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (1R,6S)-(+)-8-oxabicydo[4.3.0]nonan-7-one (9 grams) as an orange oil. The product may be further purified by distillation at reduced pressure to yield a colorless oil, $[\partial]_D = +46°$ c=1.1, chloroform. The enantiomeric excess is 98% as determined by chiral gas chromatography (Lipodex D column, column temperature 165=° C., injection temperature 180=° C., detector temperature=260° C.).

EXAMPLE 2

Alternative oxidation of cis-1,2-cyclohexane dimethanol to (1R,6S)-(+)-8-oxabicyclo[4.3.0]nonan-7-one Glycine (18.8 grams) is dissolved in 2 liters of deionized water, and the pH is adjusted by the addition of 10% sodium hydroxide to 9.0. Cis-1,2-cyclohexane dimethanol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent 1:1 ethyl acetate-methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (1R,6S)-(+)-8-oxabicyclo[4.3.0]nonan-7-one (8.5 grams) as a yellowish oil.

EXAMPLE 3

Oxidation of meso-2,3-dimethyl-1,4-butanediol to (2S,3R)-2,3-dimethylbutyrolactone Glycine (18.8 grams) is dissolved in 2 liters of deionized water, and the pH is adjusted by the addition of 10% sodium hydroxide to 9.0. Cis-1,2-cyclohexane dimethanol (10.0 grams) is added to the glycine solution with stirring until dissolution occurs, followed by the addition of β-NAD+ (Sigma, 2 grams) and flavin mononucleotide (Sigma, 30 grams). To the resulting clear orange solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent 1:1 ethyl acetate-methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by extraction with ethyl acetate (4 times 250 ml). The ethyl acetate extract is dried over anhydrous magnesium sulfate and evaporated under reduced pressure to yield (2R,3S)-2,3-dimethylbutyrolactone (9 grams) as an orange oil.

EXAMPLE 4

Alternative oxidation of meso-2,3-dimethyl-1,4-butanediol to (2S, 3R)-2,3-dimethylbutyrolactone Glycine (18.8 grams) is dissolved in 2 liters of deionized water, and the pH is adjusted by the addition of 10% sodium hydroxide to 9.0. 2,3-Dimethyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R, 3S)-2,3-dimethylbutyrolactone (8 grams) as a yellowish oil.

EXAMPLE 5
Oxidation of cis-1,2-cyclopentane dimethanol to (1R,5S)-(+)-7-oxabicyclo[3.3.0]octan-6-one Glycine (18.8 grams) is dissolved in 2 liters of deionized water, and the pH is adjusted by the addition of 10% sodium hydroxide to 9.0. Cis-1,2-cyclopentane dimethanol (10.0 grams) is added to the glycine solution with stirring until dissolution occurs, followed by the addition of β-NAD+ (Sigma, 2 grams) and flavin mononucleotide (Sigma, 30 grams). To the resulting clear orange solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent 1:1 ethyl acetate-methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (1R,5S)-(+)-7-oxabicyclo[3.3.0]octan-6-one (9 grams) as an orange oil. The product may be further purified by distillation at reduced pressure to yield a colorless oil.

EXAMPLE 6
Alternative oxidation of cis-1,2-cyclopentane dimethanol to (1R,5S)-(+)-7-oxabicyclo[3.3.0]octan-6-one Glycine (18.8 grams) is dissolved in 2 liters of deionized water, and the pH is adjusted by the addition of 10% sodium hydroxide to 9.0. Cis-1,2-cyclopentane dimethanol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent 1:1 ethyl acetate-methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (1R,5S)-(+)-7-oxabicyclo[3.3.0]nonan-6-one (8 grams) as a yellowish oil.

EXAMPLE 7
Production of (R)-2-phenylbutyrolactone by oxidation of 2-phenyl-1,4-butanediol Glycine (18.8 grams) is dissolved in 2 liters of deionized water, and the pH is adjusted by the addition of 10% sodium hydroxide to 9.0. 2-Phenyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide.

Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (R)-2-phenylbutyrolactone as a yellowish solid.

EXAMPLE 8
Production of (R)-2-benzylbutyrolactone by oxidation of 2-benzyl-1,4-butanediol Glycine (18.8 grams) is dissolved in 2 liters of deionized water, and the pH is adjusted by the addition of 10% sodium hydroxide to 9.0. 2-Benzyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (R)-2-benzylbutyrolactone as a yellowish solid.

EXAMPLE 9
Production of (2R)-2-(3-fluoropropyl)butyrolactone by oxidation of 2-(3-fluoropropyl)-1,4-butanediol Glycine (18.8 grams) is dissolved in 2 liters of deionized water, and the pH is adjusted by the addition of 10% sodium hydroxide to 9.0. 2-(3-fluoropropyl)-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-(3-fluoropropyl)butyrolactone as a yellowish oil.

EXAMPLE 10
Production of (2R)-2-imidazoylbutyrolactone by oxidation of 2-imidazoyl-1,4-butanediol Glycine (18.8 grams) is dissolved in 2 liters of deionized water, and the pH is adjusted by the addition of 10% sodium hydroxide to 9.0. 2-Imidazoyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-imidazoylbutyrolactone as a yellowish solid.

EXAMPLE 11
Production of (2R)-2 (4-fluorophenyl)butyrolactone by oxidation of 2-(4-fluorophenyl)-1,4-butanediol Glycine (18.8 grams) is dissolved in 2 liters of deionized water, and the pH is adjusted by the addition of 10% sodium hydroxide to 9.0. 2-(4-fluorophenyl)-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10,% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-(4-fluorophenyl)butyrolactone as a yellowish solid.

EXAMPLE 12
Production of (2R)-2 cyclohexylbutyrolactone by oxidation of 2-cyclohexyl-1,4-butanediol Glycine (18.8 grams) is dissolved in 2 liters of deionized water, and the pH is adjusted by the addition of 10% sodium hydroxide to 9.0. 2-Cyclohexyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-cyclohexylbutyrolactone as a yellowish solid.

EXAMPLE 13
Production of (2R)-2(4-methoxyphenyl)butyrolactone by oxidation of 2-(4-methoxyphenyl)-1,4-butanediol Glycine (18.8 grams) is dissolved in 2 liters of deionized water, and the pH is adjusted by the addition of 10% sodium hydroxide to 9.0. 2-(4-methoxyphenyl)-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-(4-methoxyphenyl)butyrolactone as a yellowish solid.

EXAMPLE 14
Production of (2R)-2 (3,4-dimethoxyphenyl)butyrolactone by oxidation of 2-(3,4-dimethoxyphenyl)-1,4-butanediol Glycine (18.8 grams) is dissolved in 2 liters of deionized water, and the pH is adjusted by the addition of 10% sodium hydroxide to 9.0. 2-(3,4-dimethoxyphenyl)-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-(3, 4-dimethoxyphenyl)butyrolactone as a yellowish solid.

EXAMPLE 15
Production of (2R)-2 (4-carboxyphenyl)butyrolactone by oxidation of 2-(4-carboxyphenyl)-1,4-butanediol Glycine (18.8 grams) is dissolved in 2 liters of deionized water, and the pH is adjusted by the addition of 10% sodium hydroxide to 9.0. 2-(4-carboxyphenyl)-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-(4-carboxyphenyl)butyrolactone as a yellowish solid.

EXAMPLE 16
Oxidation of meso-2,3-bis-carboxymethyl-1,4-butanediol to (2R, 3S)-2,3-bis-carboxymethylbutyrolactone Glycine (18.8 grams) is dissolved in 2 liters of deionized water, and the pH is adjusted by the addition of 10% sodium hydroxide to 9.0. 2,3-bis-carboxymethyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R, 3S)-2, 3-bis-carboxymethylbutyrolactone (8 grams) as a yellowish solid.

EXAMPLE 17
Conversion of (1R,6S)-(+)-8-oxabicyclo[4.3.0]nonan-7-one to (1S,2R)-2-hydroxymethyl-1-cyclohexanecarboxylate hydroxamic acid (1R,6S)-(+)-8-oxabicydo[4.3.0]nonan-7-one (1 gram) was dissolved in 5 ml of absolute ethanol, followed by the addition of 0.5 gram of hydroxylamine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (1S,2R)-2-hydroxymethyl-1-cyclohexanecarboxylate.

EXAMPLE 18
Enzymatic production of the hydroxamic acid of (1S,2R)-2-hydroxymethyl-1-cyclohexanecarboxylate (1R,6S)-(+)-8-oxabicyclo[4.3.0]nonan-7-one (1 gram) was dissolved in 5 ml of t-butyl methyl ether, followed by the addition of 0.5 gram of hydroxylamine. Lipase from Candida rugosa (0.5 g, Sigma L1754) was added, and the progress of the reaction was followed by thin layer chromatography. After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (1S,2R)-2-hydroxymethyl-1-cyclohexane-carboxylate.

EXAMPLE 19
Conversion of (1R,5S)-(+)-7-oxabicyclo[3.3.0]octan-6-one to (1S,2R)-2-hydroxymethyl-1-cyclopentanecarboxylic hydroxamic acid (1R,5S)-(+)-7-oxabicyclo[3.3.0]octan-6-one (1 gram) was dissolved in 5 ml of absolute ethanol, followed by the addition of 0.5 gram of hydroxylamine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (1S,2R)-2-hydroxymethyl-1-cylopentanecarboxylate.

EXAMPLE 20
Enzymatic production of the hydroxamic acid of (1S,2R)-2-hydroxymethyl-1-cyclopentanecarboxylate (1R,5S)-(+)-7-oxabicyclo[3.3.0]octan-6-one (1 gram) was dissolved in 5 ml of t-butyl methyl ether, followed by the addition of 0.5 gram of hydroxylamine. Lipase from Candida rugosa (0.5 g, Sigma L1754) was added, and the progress of the reaction was followed by thin layer chromatography. After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (1S,2R)-2-hydroxymethyl-1-cyclopentane-carboxylate.

EXAMPLE 21
Conversion of (2S,3R)-2,3-dimethylbutyrolactone to (2S, 3R)-2,3-dimethyl-4-hydroxybutanoate hydroxamic acid (2S,3R)-2,3-dimethylbutyrolactone (1 gram) was dissolved in 5 ml of absolute ethanol, followed by the addition of 0.5 gram of hydroxylamine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (2S,3R)-2,3-dimethyl-4-hydroxybutanoate.

EXAMPLE 22
Enzymatic production of the hydroxamic acid of (2S,3R)-2,3-dimethyl-4-hydroxybutanoate (2S,3R)-2,3-dimethylbutyrolactone (1 gram) was dissolved in 5 ml of t-butyl methyl ether, followed by the addition of 0.5 gram of hydroxylamine. Lipase from Candida rugosa (0.5 g, Sigma L1754) was added, and the progress of the reaction was followed by thin layer chromatography. After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (2S,3R)-2,3-dimethyl-4-hydroxybutanoate.

EXAMPLE 23
Conversion of (1R,6S)-(+)-8-oxabicyclo[4.3.0]nonan-7-one to the (1S,2R)-2-hydroxymethyl-1-cyclohexanecarboxylic hydrazide (1R,6S)-(+)-oxabicyclo[4.3.0]nonan-7-one (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with lo HCl, and the ethyl acetate solution was dried over MgSO$_4$, filtered, and rotary evaporated to leave 0.9 grams of the hydrazide of (1S,2R)-2-hydroxymethyl-1-cyclohexanecarboxylate.

EXAMPLE 24
Conversion of (1R,5S)-(+)-7-oxabicyclo[3.3.0]octan-6-one to (1S,2R)-2-hydroxymethyl-1-cyclopentanecarboxylic hydrazide (1R,5S)-(+)-7-oxabicyclo[3.3.0]octan-6-one (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (1S,2R)-2-hydroxymethyl-1-cyclopentanecarboxylate.

EXAMPLE 25
Conversion of (2S, 3R)-2,3-dimethylbutyrolactone to (2S, 3R)-2,3-dimethyl-4-hydroxybutanoic hydrazide (2S, 3R)-2,3-dimethylbutyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (2S,3R)-2,3-dimethyl-4-hydroxybutanoic acid.

EXAMPLE 26
Conversion of (1R,6S)-(+)-8-oxabicyclo[4.3.0]nonan-7-one to (1S,2R)-2-hydroxymethyl-1-cyclohexanecarboxamide (1R,6S)-(+)-8-oxabicyclo[4.3.0]nonan-7-one (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over MgSO$_4$, filtered, and rotary evaporated to leave 0.7 grams of (1S,2R)-2-hydroxymethyl-1-cyclohexanecarboxamide.

EXAMPLE 27
Conversion of (1R,5S)-(+)-7-oxabicyclo[3.3.0]octan-6-one to (1S,2R)-2-hydroxymethyl-1-cyclopentanecarboxamide (1R,5S)-(+)-7-oxabicyclo[3.3.0]octan-6-one (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over MgSO$_4$, filtered, and rotary evaporated to leave 0.7 grams of (1S,2R)-2-hydroxymethyl-1-cyclopentanecarboxamide.

EXAMPLE 28
Conversion of (2S,3R)-2,3-dimethylbutyrolactone to the (2S,3R)-2,3-dimethyl-4-hydroxybutyramide (2S,3R-2,3-dimethylbutyrolactone (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over $MgSO_4$, filtered, and rotary evaporated to leave 0.7 grams of (2S,3R)-2,3-dimethyl-4-hydroxybutyramide.

EXAMPLE 29
Conversion of (R)-2-phenylbutyrolactone to the (R)-2-phenyl-4-hydroxybutyramide (R)-2-phenylbutyrolactone (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over $MgSO_4$, filtered, and rotary evaporated to leave 0.7 grams of (R)-2-phenyl-4-hydroxybutyramide.

EXAMPLE 30
Conversion of (R)-2-benzylbutyrolactone to the (R)-2-benzyl-4-hydroxybutyramide (R)-2-benzylbutyrolactone (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over $MgSO_4$, filtered, and rotary evaporated to leave 0.7 grams of (R)-2-benzyl-4-hydroxybutyramide.

EXAMPLE 31
Conversion of (R)-2-phenylbutyrolactone to (R)-2-phenyl-4-hydroxybutanoic acid hydrazide (R)-2-phenylbutyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over $MgSO_4$, filtered, and rotary evaporated to leave 0.9 grams of the hydrazide of (R)-2-phenyl-4-hydroxybutanoic acid.

EXAMPLE 32
Conversion of (R)-2-benzylbutyrolactone to (R)-2-benzyl-4-hydroxybutanoic acid hydrazide (R)-2-benzylbutyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over $MgSO_4$, filtered, and rotary evaporated to leave 0.9 grams of the hydrazide of (R)-2-benzyl-4-hydroxybutanoic acid.

EXAMPLE 33
Conversion of (R)-2-(4-fluorophenyl)butyrolactone to (R)-2-(4-fluorophenyl)-4-hydroxybutanoic acid hydrazide (R)-2-(4-fluorophenyl)butyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over $MgSO_4$, filtered, and rotary evaporated to leave 0.9 grams of the hydrazide of (R)-2-(4-fluorophenyl)-4-hydroxybutanoic acid.

EXAMPLE 34
Conversion of (S)-2-phenylbutyrolactone to the (S)-2-phenyl-4-hydroxybutyramide (S)-2-phenylbutyrolactone (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over $MgSO_4$, filtered, and rotary evaporated to leave 0.7 grams of (S)-2-phenyl-4-hydroxybutyramide.

EXAMPLE 35
Conversion of (S)-2-benzylbutyrolactone to the (S)-2-benzyl-4-hydroxybutyramide (S)-2-benzylbutyrolactone (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over $MgSO_4$, filtered, and rotary evaporated to leave 0.7 grams of (S)-2-benzylhydroxybutyramide.

EXAMPLE 36
Conversion of (S)-2-phenylbutyrolactone to (S)-2-phenyl-4-hydroxybutanoic acid hydrazide (S)-2-phenylbutyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over $MgSO_4$, filtered, and rotary evaporated to leave 0.9 grams of the hydrazide of (S)-2-phenyl-4-hydroxybutanoic acid.

EXAMPLE 37
Conversion of (S)-2-benzylbutyrolactone to (S)-2-benzyl-4-hydroxybutanoic acid hydrazide (S)-2-benzylbutyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over $MgSO_4$, filtered, and rotary evaporated to leave 0.9 grams of the hydrazide of (S)-2-benzylhydroxybutanoic acid.

EXAMPLE 38
Conversion of (S)-2-(4-fluorophenyl)butyrolactone to (S)-2-(4-fluorophenyl)-4-hydroxybutanoic acid hydrazide (S)-2-(4-fluorophenyl)butyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over $MgSO_4$, filtered, and rotary evaporated to leave 0.9 grams of the hydrazide of (S)-2-(4-fluorophenyl)-4-hydroxybutanoic acid.

EXAMPLE 39
Production of (1S,2R)-1-amino-2-(hydroxymethyl)cyclohexane by Hofmann Rearrangement of (1S,2R)-2-hydroxymethyl-1-cyclohexanecarboxamide Ten grams of (1S,2R)-2-hydroxymethyl-1-cyclohexanecarboxamide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether×250 ml), and the extracts dried over $MgSO_4$, filtered, and the solvent removed by rotary evaporation. The product (1S,2R)-1-amino-2-(hydroxymethyl)cyclohexane is isolated as a light yellow oil.

EXAMPLE 40
Production of (1S,2R)-1-amino-2-(benzoyloxymethyl)cyclohexane by Lossen Rearrangement of (1S,2R)-2-hydroxymethyl-1-cyclohexanecarboxylate hydroxamic acid Ten grams of (2R,3S)-2-methyl-3-hydroxybutyrohydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over $MgSO_4$, filtered, and the solvent removed by rotary evaporation. The product (1S,2R)-1-amino-2-(benzoyloxymethyl)cyclohexane is isolated as a light yellow solid.

EXAMPLE 41
Production of (1S,2R)-1-amino-2-(hydroxymethyl)cyclohexane by Curtius Rearrangement of (1S,2R)-2-hydroxymethyl-1-cyclohexanecarboxylate hydrazide The hydrazide of (1S,2R)-2-hydroxymethyl-1-cyclohexanecarboxylic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (1S,2R)-1-amino-2-(hydroxymethyl)cyclohexane is isolated as a light yellow oil.

EXAMPLE 42
Production of (1S,2R)-1-amino-2-(hydroxymethyl)cyclopentane by Hofmann Rearrangement of (1S,2R)-2-hydroxymethyl-1-cyclopentanecarboxamide Ten grams of (1S,2R)-2-hydroxymethyl-1-cyclopentanecarboxamide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether×250 ml), and the extracts dried over $MgSO_4$, filtered, and the solvent removed by rotary evaporation. The product (1S,2R)-1-amino-2-(hydroxymethyl)cyclopentane is isolated as a light yellow oil.

EXAMPLE 43
Production of (1S,2R)-1-amino-2-(benzoyloxymethyl)cyclopentane by Lossen Rearrangement of (1S,2R)-2-hydroxymethyl-1-cyclopentanecarboxylate hydroxamic acid Ten grams of (1S,2R)-2-hydroxymethyl-1-cyclopentanecarboxylate hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over $MgSO_4$, filtered, and the solvent removed by rotary evaporation. The product (1S,2R)-1-amino-2-(benzoyloxymethyl)cyclopentane is isolated as a light yellow solid.

EXAMPLE 44
Production of (1S,2R)-1-amino-2-(hydroxymethyl)cyclopentane by Curtius Rearrangement of (1S,2R)-2-hydroxymethyl-1-cyclohexanecarboxylate hydrazide The hydrazide of (1S,2R)-2-hydroxymethyl-1-cyclohexanecarboxylic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (1S,2R)-1-amino-2-(hydroxymethyl)cyclopentane is isolated as a light yellow oil.

EXAMPLE 45
Production of (2S,3S)-2-methyl-3-aminobutanol by Hofmann Rearrangement of (2S,3R)-2,3-dimethyl-4-hydroxybutyramide Ten grams of (2S,3R)-2,3-dimethyl-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether×250 ml), and the extracts dried over $MgSO_4$, filtered, and the solvent removed by rotary evaporation. The product (2S,3S)-2-methyl-3-aminobutanol is isolated as a light yellow oil.

EXAMPLE 46
Production of (2S,3S)-2-methyl-3-aminobutanol benzoate ester by Lossen Rearrangement of (2S,3R)-2,3-dimethyl-4-hydroxybutanoic hydroxamic acid Ten grams of (2S,3R)-2,3-dimethyl-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over $MgSO_4$, filtered, and the solvent removed by rotary evaporation. The product (2S,3S)-2-methyl-3-aminobutanol benzoate ester is isolated as a light yellow solid.

EXAMPLE 47
Production of (2S,3S)-2-methyl-3-aminobutanol by Curtius Rearrangement of (2S,3R)-2,3-dimethyl-4-hydroxybutanoic acid hydrazide The hydrazide of (2S,3R)-2,3-dimethylthydroxybutanoic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (2S,3S)-2-methyl-3-aminobutanol is isolated as a light yellow oil.

EXAMPLE 48
Production of (R)-1-phenyl-3-hydroxypropylamine by Hofmann Rearrangement of (R)-2-phenyl-4-hydroxybutyramide Ten grams of (R)-2-phenyl-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether×250 ml), and the extracts dried over $MgSO_4$, filtered, and the solvent removed by rotary evaporation. The product (R)-1-phenyl-3-hydroxypropylamine is isolated as a light yellow oil.

EXAMPLE 49
Production of (R)-1-phenyl-3-hydroxypropylamine benzoate ester by Lossen Rearrangement of (R)-2-phenyl-4-hydroxybutanoic hydroxamic acid Ten grams of (R)-2-phenyl-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over $MgSO_4$, filtered, and the solvent removed by rotary evaporation. The product (R)-1-phenyl-3-hydroxypropylamine benzoate ester is isolated as a light yellow solid.

EXAMPLE 50
Production of (R)-1-phenyl-3-hydroxypropylamine by Curtius Rearrangement of (R)-2-phenyl-4-hydroxybutanoic acid hydrazide The hydrazide of (R)-2-phenyl-4-hydroxybutanoic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (R)-1-phenyl-3-hydroxypropylamine is isolated as a light yellow oil.

EXAMPLE 51
Production of (S)-1-phenyl-3-hydroxypropylamine by Hofmann Rearrangement of (S)-2-phenyl-4-hydroxybutyramide Ten grams of (S)-2-phenyl-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether×250 ml), and the extracts dried over $MgSO_4$, filtered, and the solvent removed by rotary evaporation. The product (S)-1-phenyl-3-hydroxypropylamine is isolated as a light yellow oil.

EXAMPLE 52
Production of (S)-1-phenyl-3-hydroxypropylamine benzoate ester by Lossen Rearrangement of (S)-2-phenyl-4-hydroxybutanoic hydroxamic acid Ten grams of (S)-2-phenyl-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over $MgSO_4$, filtered, and the solvent removed by rotary evaporation. The product (S)-1-phenyl-3-hydroxypropylamine benzoate ester is isolated as a light yellow solid.

EXAMPLE 53
Production of (S)-1-phenyl-3-hydroxypropylamine by Curtius Rearrangement of (S)-2-phenyl-4-hydroxybutanoic acid hydrazide The hydrazide of (S)-2-phenyl-hydroxybutanoic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (S)-1-phenyl-3-hydroxypropylamine is isolated as a light yellow oil.

EXAMPLE 54
Production of (R)-1-benzyl-3-hydroxypropylamine by Hofmann Rearrangement of (R)-2-benzyl-4-hydroxybutyramide Ten grams of (R)-2-benzyl-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether×250 ml), and the extracts dried over $MgSO_4$, filtered, and the solvent removed by rotary evaporation. The product (R)-1-benzyl-3-hydroxypropylamine is isolated as a light yellow oil.

EXAMPLE 55
Production of (R)-1-benzyl-3-hydroxypropylamine benzoate ester by Lossen Rearrangement of (R)-2-benzyl-4-hydroxybutanoic hydroxamic acid Ten grams of (R)-2-benzyl-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over $MgSO_4$, filtered, and the solvent removed by rotary evaporation. The product (R)-1-benzyl-3-hydroxypropylamine benzoate ester is isolated as a light yellow solid.

EXAMPLE 56
Production of (R)-1-benzyl-3-hydroxypropylamine by Curtius Rearrangement of (R)-2-benzyl-4-hydroxybutanoic acid hydrazide The hydrazide of (R)-2-benzyl-hydroxybutanoic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (R)-1-benzyl-3-hydroxypropylamine is isolated as a light yellow oil.

EXAMPLE 57
Production of (S)-1-benzyl-3-hydroxypropylamine by Hofmann Rearrangement of (S)-2-benzyl-4-hydroxybutyramide Ten grams of (S)-2-benzyl-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether×250 ml), and the extracts dried over $MgSO_4$, filtered, and the solvent removed by rotary evaporation. The product (S)-1-benzyl-3-hydroxypropylamine is isolated as a light yellow oil.

EXAMPLE 58
Production of (S)-1-benzyl-3-hydroxypropylamine benzoate ester by Lossen Rearrangement of (S)-2-benzyl-4-hydroxybutanoic hydroxamic acid Ten grams of (S)-2-benzyl-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over $MgSO_4$, filtered, and the solvent removed by rotary evaporation. The product (S)-1-benzyl-3-hydroxypropylamine benzoate ester is isolated as a light yellow solid.

EXAMPLE 59
Production of (S)-1-benzyl-3-hydroxypropylamine by Curtius Rearrangement of (S)-2-benzyl-4-hydroxybutanoic acid hydrazide The hydrazide of (S)-2-benzyl-4-hydroxybutanoic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (S)-1-benzyl-3-hydroxypropylamine is isolated as a light yellow oil.

EXAMPLE 60
Production of (R)-1-(4-fluorophenyl)-3-hydroxypropylamine by Hofmann Rearrangement of (R)-2-(4-fluorophenyl)-4-hydroxybutyramide Ten grams of (R)-2-(4-fluorophenyl)-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether×250 ml), and the extracts dried over $MgSO_4$, filtered, and the solvent removed by rotary evaporation. The product (R)-1-(4-fluorophenyl)-3-hydroxypropylamine is isolated as a light yellow oil.

EXAMPLE 61
Production of (R)-1-(4-fluorophenyl)-3-hydroxypropylamine benzoate ester by Lossen Rearrangement of (R)-2-(4-fluorophenyl)-4-hydroxybutanoic hydroxamic acid Ten grams of (R)-2-(4-fluorophenyl)-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over $MgSO_4$, filtered, and the solvent removed by rotary evaporation. The product (R)-1-(4-fluorophenyl)-3-hydroxypropylamine benzoate ester is isolated as a light yellow solid.

EXAMPLE 62
Production of (R)-1-(4-fluorophenyl)-3-hydroxypropylamine by Curtius Rearrangement of (R)-2-(4-fluorophenyl)-4-hydroxybutanoic acid hydrazide The hydrazide of (R)-2-(4-fluorophenyl)-4-hydroxybutanoic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (R)-1-(4-fluorophenyl)-3-hydroxypropylamine is isolated as a light yellow oil.

EXAMPLE 63
Production of (S)-1-(4-fluorophenyl)-3-hydroxypropylamine by Hofmann Rearrangement of (S)-2-(4-fluorophenyl)-4-hydroxybutyramide Ten grams of (S)-2-(4-fluorophenyl)-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether×250 ml), and the extracts dried over $MgSO_4$, filtered, and the solvent removed by rotary evaporation. The product (S)-1-(4-fluorophenyl)-3-hydroxypropylamine is isolated as a light yellow oil.

EXAMPLE 64
Production of (S)-1-(4-fluorophenyl)-3-hydroxypropylamine benzoate ester by Lossen Rearrangement of (S)-2-(4-fluorophenyl)-4-hydroxybutanoic hydroxamic acid Ten grams of (S)-2-(4-fluorophenyl)-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over MgSO$_4$, filtered, and the solvent removed by rotary evaporation. The product (S)-1-(4-fluorophenyl)-3-hydroxypropylamine benzoate ester is isolated as a light yellow solid.

EXAMPLE 65

Production of (S)-1-(4-fluorophenyl)-3-hydroxypropylamine by Curtius Rearrangement of (S)-2-(4-fluorophenyl)-4-hydroxybutanoic acid hydrazide The hydrazide of (S)-2-(4-fluorophenyl)-4-hydroxybutanoic acid (0.5 gram) is reacted with a solution of 0.5 grams of sodium nitrite in 10 ml of 5% H$_2$SO$_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over MgSO$_4$, filtration, and the removal of solvent by rotary evaporation. The product (S)-1-(4-fluorophenyl)-3-hydroxypropylamine is isolated as a light yellow oil.

What is claimed is:

1. A compound represented by the formula

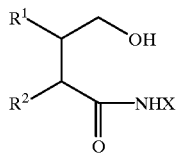

wherein X is NH$_2$ and R$^1$ and R$^2$ are independently chosen from the group consisting of hydrogen, alkenyl, cycloalkenyl, alkynyl, aryl, aralkenyl, and heterocyclic ring system, except that R$_1$ and R$_2$ are not both hydrogen, with the provisos that (1) when R$^1$ is H, R$^2$ is not phenyl or benzyl; and (2) when R$^2$ is H, R$^1$ is not benzyl.

2. A compound according to claim 1 which consists substantially of a single stereoisomer.

3. A compound according to claim 1 which comprises at least about 98% of a single stereoisomer.

4. A compound according to claim 1, wherein the compound is 2-(4-fluorophenyl)-4-2-hydroxybutanoic acid hydrazide.

5. A compound according to claim 1, wherein at least one of R$^1$ and R$^2$ is substituted aryl.

6. A compound according to claim 1, wherein at least one of R$^1$ and R$^2$ is substituted phenyl.

7. A compound according to claim 1, wherein R$^1$ is not hydrogen.

8. A compound according to claim 1, wherein R$^2$ is not hydrogen.

9. A compound according to claim 1, wherein R$^1$ is selected from the group consisting of hydrogen, alkenyl, cycloalkenyl, alkynyl, aralkyl, aralkenyl, and heterocyclic ring system.

10. A compound represented by the formula

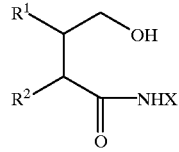

wherein:

X is NH$_2$;

R$^1$ is selected from the group consisting of hydrogen, alkyl, alkenyl, cycloalkyl, cycloalkylalkyl, cycloalkenyl, cycloalkenylalkyl, alkynyl, aryl, aralkyl, aralkenyl, and heterocyclic ring system; and R$^2$ is selected from the group consisting of hydrogen, alkenyl, cycloalkyl, cycloalkenyl, cycloalkenylalkyl, alkynyl, aryl, aralkyl, aralkenyl, and heterocyclic ring system;

except that R$_1$ and R$_2$ are not both hydrogen, and with the provisos that (1) when R$^1$ is H, R$^2$ is not phenyl or benzyl; and (2) when R$^2$ is H, R$^1$ is not benzyl.

11. A compound according to claim 10, wherein R$^2$ is selected from the group consisting of hydrogen, alkenyl, cycloalkyl, cycloalkenyl, alkynyl, aryl, aralkyl, aralkenyl, and heterocyclic ring system.

12. A compound according to claim 10, wherein R$^2$ is selected from the group consisting of hydrogen, alkenyl, cycloalkenyl, alkynyl, aryl, aralkyl, aralkenyl, and heterocyclic ring system.

13. A compound according to claim 10, wherein R$^2$ is substituted aryl.

14. A compound according to claim 10, wherein R$^2$ is substituted phenyl.

* * * * *